US006787348B1

(12) United States Patent
Kringelum et al.

(10) Patent No.: US 6,787,348 B1
(45) Date of Patent: Sep. 7, 2004

(54) LIQUID STARTER CULTURES HAVING IMPROVED STORAGE STABILITY AND USE THEREOF

(75) Inventors: Boerge Kringelum, Ballerup (DK); Lene Kragelund, Frederiksberg (DK)

(73) Assignee: CHR. Hansen, Horsholm (DK)

( * ) Notice: Subject to any disclaimer, the term of this patent is extended or adjusted under 35 U.S.C. 154(b) by 0 days.

(21) Appl. No.: 09/446,400

(22) PCT Filed: Dec. 21, 1999

(86) PCT No.: PCT/DK99/00723

§ 371 (c)(1),
(2), (4) Date: Dec. 22, 1999

(87) PCT Pub. No.: WO00/39281

PCT Pub. Date: Jul. 6, 2000

Related U.S. Application Data

(60) Provisional application No. 60/113,802, filed on Dec. 23, 1998, and provisional application No. 60/145,907, filed on Jul. 27, 1999.

(30) Foreign Application Priority Data

Dec. 23, 1998 (DK) .......................................... 199801728
Jul. 27, 1999 (DK) .......................................... 199901067

(51) Int. Cl.$^7$ ................................................. C12N 1/20
(52) U.S. Cl. ............................... 435/252.9; 435/252.1; 435/252.4; 435/252.6; 435/139; 426/8; 426/34; 426/61
(58) Field of Search .......................... 435/252.9, 252.4, 435/252.1, 253.6, 139; 426/8, 34, 61

(56) References Cited

U.S. PATENT DOCUMENTS

| 3,975,545 A | | 8/1976 | Vedamuthu |
| 4,588,595 A | * | 5/1986 | Okonogi et al. |
| 4,834,987 A | * | 5/1989 | Lembke et al. |
| 4,870,020 A | * | 9/1989 | Sozzi |
| 5,453,286 A | * | 9/1995 | Castberg et al. |

FOREIGN PATENT DOCUMENTS

| DD | 121 800 A | 8/1976 |
| EP | 0 130 775 | 9/1985 |
| EP | 0 196 593 A2 | 10/1986 |
| EP | 0 220 548 A | 5/1987 |
| EP | 0 220 548 A2 | 5/1987 |
| EP | 0 414 404 A2 | 2/1991 |
| EP | 0 443 653 A1 | 8/1991 |
| WO | WO 91/11509 | 8/1991 |
| WO | WO 98/54337 | 12/1998 |

OTHER PUBLICATIONS

Bannikova L A et al.: "Starter for cows milk koumiss." Trudy, Vsesoyuznyi, Nauchno–Issledovatel Skii Institut, Molochnoi Promyshlennosti, vol. 27, 1970, XP002136043, Vses. Nauchno–issled. Inst. Molochnoi Prom Moscow, USSR, English abstract.

Cowman R A et al.; "Ultra–low temperature storage of lactic streptococci"; Journal of Dairy Science, vol. 48, 1965, pp. 1531–1532, XP000892053, table 1.
Database FSTA/IFIS [Online], International Food Information Service (IFIS), Franfurt/Main, DE, AN 84–2–09–p1932, 1982, Borcherds K B: "Commercial starter manufacture and future developments"; XP002137335; English abstract.
Galesloot, TH. E. et al., "Symbiosis in yoghurt (1). Stimulation of *Lactobacillus bulgaricus* by a factor produced by *Streptococcus thermophilus*", Netherlands Milk and Dairy Journal, vol. 22, No. 1/2, 1968, pp. 50–63, XP00212897.
Veringa H. A., et al., "Symbiosis in yoghurt (II). Isolation and identification of a growth factor for *Lactabacillus bulgaricus* produced by *Streeptococcus thermophilus*", Netherlands Milk and Dairy Journal, vol. 22, No. 3, 1968, pp. 114–120, XP002120898.
Suzuki, I. et al., "Growth of *Lactobacillus bulgaricus* in milk 1. Cell elongation and the role of formic acid in boiled milk", J. Dairy Sci, (1968) 69 (2), 311–320, XP002120903.
Dahiya, Raghunath S. et al., "Growth of streptococcus starter cultures in milk fortified with nucleric acid derivatives", J. Dairy Sci. (1964), 47(4), 374–7, XP002120896.
Varga, L. (1) et al., "Effect of a *Spirulina platensis* biomass and that of its active components on single strains of dairy starter cultures", Milchwissenschaft, vol. 54, No. 4, pp. 187–190, Apr. 1999, XP002120900.
Auclair, J.E. et al., "Formic acid as growth stimulant for *Lactobacillus lactis* in autoclaved milk", Nature, vol. 179, 1957, pp. 782–783, XP002120901.
Pulusani, S.R. et al., "Stimulation by formate of antimicrobial activity of *Lactobacillus bulgaricus* in milk", Journal of Food Science, vol. 49, 1984, pp. 652–653, XP002120902.
Moreira, Maria R. et al., "Sodium formate stimulation of the proteolytic activity of lactobacilli grown at low temperature", Milchwissenschart, (1997), vol. 52, No. 11, pp. 607–610, XP002120904.
Gilliland, S.E., "Preparation and storage of concentrated cultures of lactic streptococci", Journal of Dairy Science, vol. 60, No. 5, 1977, pp. 805–809, XP002120906.
Gilliland, S.E. et al., "Frozen concentrated cultures of lactic starter bacteria. A review", Journal of Milk and Food Technology, vol. 37, No. 2, 1974, pp. 107–111, XP002120907.
L. Foldager, Determination of acidification activity in F–DVS by the LF method, Oct. 3, 1994.
International Search Report for PCT/DK 99/00723.
Cahalan, D. and Genigeorgis, C., Preervation methods for lactic starter cultures, Abstracts of the Annual Meeting of the American society for Microbiology, 1978 (XP–002146211) (Abstract).

* cited by examiner

*Primary Examiner*—Leon B. Lankford, Jr.
(74) *Attorney, Agent, or Firm*—Hunton & Williams LLP

(57) ABSTRACT

Liquid microbial starter culture that retains its initial metabolic activity during storage for extended periods of time. Such liquid starter cultures are useful in the manufacturing of food and feed products. Starter cultures of the invention include culture of lactic acid bacteria, e.g. Lactococcus species.

26 Claims, 5 Drawing Sheets

LIQUID STARTER CULTURES HAVING IMPROVED STORAGE STABILITY AND USE THEREOF

This application is a 371 of PCT/DK99/00723 filed Dec. 21, 1999, which claims benefit of No. 60/113,802 filed Dec. 23, 1998, which claims benefit of No. 60/145,907 filed Jul. 27, 1999.

FIELD OF INVENTION

The present invention relates to the field of microbial starter cultures and in particular there are provided liquid starter cultures that retain their initial metabolic activity during storage for extended periods of time. Such liquid starter cultures are useful in the manufacturing of food and feed products.

TECHNICAL BACKGROUND

Microorganisms are involved in the manufacture of food and feed products including most dairy products. Thus, bacterial cultures, in particular cultures of bacteria that are generally classified as lactic acid bacteria are essential in the making of all fermented milk products, cheese and butter. Cultures of such bacteria are referred to as starter cultures and they impart specific features to various dairy products by performing a number of functions.

Commercial dairy starter cultures are generally composed of lactic acid and citric acid-fermenting lactic acid bacteria. In the present context, the expression "lactic acid bacteria" designates a group of Gram positive, catalase negative, non-motile, microaerophilic or anaerobic bacteria which ferment sugar with the production of acids including lactic acid as the predominantly produced acid, acetic acid, formic acid and propionic acid. The industrially most useful lactic acid bacteria are found among Lactococcus species, Streptococcus species, Enterococcus species, Lactobacillus species, Leuconostoc species and Pediococcus species.

Commonly used dairy starter culture strains of lactic acid bacteria are generally divided into mesophilic organisms having optimum growth temperatures at about 30° C. and thermophilic organisms having optimum growth temperatures in the range of about 40 to about 45° C. Typical organisms belonging to the mesophilic group include *Lactococcus lactis* subsp. *lactis, Lactococcus lactis* subsp. *cremoris, Leuconostoc mesenteroides* subsp. *cremoris, Pediococcus pentosaceus, Lactococcus lactis* subsp. *lactis* biovar. *diacetylactis* and *Lactobacillus casei* subsp. *casei*. Thermophilic lactic acid bacterial species include as examples *Streptococcus thermophilus, Enterococcus faecium, Lactobacillus lactis, Lactobacillus helveticus, Lactobacillus delbrueckii* subsp. *bulgaricus* and *Lactobacillus acidophilus*.

Also the strict anaerobic bacteria belonging to the genus Bifidobacterium including *Bifidobacterium bifidum* and *Bifidobacterium longum* are commonly used as dairy starter cultures and are generally included in the group of lactic acid bacteria. Additionally, species of Propionibacterium are used as dairy starter cultures, in particular in the manufacture of cheese.

Additionally, organisms belonging to the Brevibacterium genus are commonly used as food starter cultures.

Another group of microbial starter cultures is fungal cultures, including yeast cultures and cultures of filamentous fungi, which are particularly used in the manufacture of certain types of cheese and beverage. Examples of currently used cultures of fungi include *Penicillium roqueforti, Penicillium candidum, Geotrichum candidum, Torula kefir, Saccharomyces kefir* and *Saccharomyces cerevisiae*.

Presently, commercial starter cultures are commonly distributed as frozen concentrates. Under these conditions, the viability of the cultures is preserved for extended periods of time and the cultures can be inoculated directly into milk without intermediate transfer. Such cultures are generally referred to as direct vat set (DVS)-cultures. Another presentation of commercial DVS-starter cultures is as freeze-dried or lyophilised cultures in the form of a powder. In this form, the starter can be shipped without refrigeration, but storage below freezing temperature is recommended.

Although commercial starters thus are available as cultures, which can be added directly to milk without any intermediate transfer or propagation, it is not uncommon that dairies produce in-house bulk starters at regular intervals depending on the requirement. A "bulk starter" is defined herein as a starter culture propagated at the dairy plant for inoculation into milk. Such bulk starters are generally made by inoculating heat treated milk with a volume of a previous bulk starter or with a freeze-dried or frozen starter culture preparation, followed by incubating the thus inoculated milk under conditions permitting the starter culture strain(s) to propagate for a sufficient period of time to provide a desired cell number. The incubation period is typically in the range of 4 to 24 hours.

However, the preparation of such bulk starter cultures is labour intensive and it occupies much space and equipment, and there is a considerable risk of contamination with spoilage bacteria and/or phages during the step of propagation.

The use of commercial liquid starter cultures in the food and feed manufacturing industry including the dairy industry has been suggested as a useful alternative to the use of commercial frozen and freeze-dried starter cultures. The advantages for the industry by having such liquid starter cultures at its disposal would be several. Thus, it would be highly convenient and much less labour consuming to handle such starter cultures at food and feed manufacturing plants as compared to the use of the conventional frozen or freeze-dried cultures. Thus, when using liquid starter cultures, the inoculation of the material to be inoculated can be made directly e.g. by connecting the container with the liquid culture directly to the process line, thus avoiding the tedious work connected with opening several packagings of culture prior to inoculation. Additionally, it can be avoided to open the process line, as it is required when using frozen or freeze-dried cultures, which reduces the risk of contamination.

However, the use of commercial liquid starter cultures has so far not been feasible or possible, as such cultures, even if the cells of the cultures keep their viability, rapidly loose their metabolic activity such as e.g. their acid-producing (acidification) activity when kept stored even for shorter periods of time. To be commercially useful, liquid starter cultures should preferably retain their metabolic activity for at least 1 week and more, preferably for at least 2–3 weeks. Up till now it has not been possible to provide commercial liquid starter cultures having such a high stability.

It is therefore an important objective of the present invention to provide liquid starter cultures which show a high degree of storage stability in respect of retaining the metabolic activity when kept under cool storage conditions for extended periods of time.

SUMMARY OF THE INVENTION

Accordingly, it is the primary objective of the invention to provide commercial liquid microbial starter cultures for the manufacturing of food and feed products, which cultures can be stored at the site of food or feed manufacturing such as a dairy plant for extended periods of time without significant loss of their initial metabolic activity.

Thus, in a first aspect, the invention pertains to a liquid starter culture comprising an effective amount of a compound that has a metabolic activity stabilising effect, said starter culture retains at least 50% of its initial metabolic activity at a temperature of −20° C. or higher for 1 week or more.

In another aspect, the invention provides a liquid starter culture capable of retaining at least 50% of its initial metabolic activity at a temperature of −20° C. or higher for 1 week or more, said culture comprising at least one compound selected from the group consisting of a sugar alcohol including glycerol; carbohydrates including ascorbic acid; disaccharides including sucrose and trehalose; vitamins; antioxidants; inert gases and surfactants including Tween® compounds.

In a further aspect, there is provided a method of stabilising a liquid starter culture, the method comprising adding to the culture concentrate an effective amount of a metabolic activity stabilising compound whereby at least 50% of the initial metabolic activity of the culture concentrate is retained at a temperature of −20° C. or higher for 1 week or longer.

In a still further aspect, there is provided a method of providing a liquid starter culture as defined above, said method comprising adding to the culture an amount of at least one compound selected from the group consisting of a sugar alcohol including glycerol, carbohydrates including ascorbic acid, disaccharides including sucrose and trehalose, vitamins, antioxidants, inert gases and surfactants including Tween® compounds, said amount being sufficient to maintain the starter culture in a liquid state at a temperature in the range of −20° C. to 0° C.

In yet another aspect, the invention pertains to a method of preparing a food or a feed product said method comprising using a stabilised liquid starter culture according to the invention.

DETAILED DISCLOSURE OF THE INVENTION

It is an essential feature of the liquid starter culture which is provided herein that the starter culture can be supplied to the site of food or feed manufacturing such as a dairy plant and be stored for extended periods of time prior to use. As used herein, the expression "liquid starter culture" relates to non-frozen liquid starter cultures having a liquid phase, e.g. an aqueous phase, content that is typically in the range of 50–90% by weight.

Thus, the liquid starter culture according to the invention comprising an effective amount of at least one compound that has a metabolic activity stabilising effect, said starter culture preferably retains at least 50% of its initial metabolic activity during storage at a temperature of −20° C. or higher for 1 week or more. It is, however, preferred that the liquid starter culture retains at least 60% of its initial metabolic activity, e.g. at least 70% including at least 80% such as at least 90% of its initial metabolic activity.

As used herein the term "an effective amount" relates to an amount of a metabolic activity stabilising compound, which is added to the liquid starter culture at the starter culture production site or at the dairy plant and which is sufficient to obtain the desired stability of the culture when kept under the above conditions. The stabilising compound which is useful in the liquid starter culture according to the invention may be any compound which permits the liquid starter culture to retain its initial metabolic activity when kept for extended periods of time at a temperature above or below 0° C.

Although the acid-producing activity is exemplified herein, this invention is intended to encompass the stabilisation of any types of metabolic activities of a starter culture. Thus, the term "metabolic activity" refers to the oxygen removal activity of the starter cultures, its acid-producing activity, i.e. the production of e.g. lactic acid, acetic acid, formic acid and/or propionic acid, or its metabolite producing activity such as the production of aroma compounds such as acetaldehyde, α-acetolactate, acetoin, diacetyl and 2,3-butylene glycol (butanediol). It will be understood that the expression "initial metabolic activity" refers to the metabolic activity of the starter organism prior to storage. In addition, it will be appreciated that the "initial metabolic activity" of the liquid starter culture is determined as described in the below Examples or any other known method of determining the production of metabolites of microbial cultures. Furthermore, the expression "retaining its initial metabolic activity" is used interchangeably with the expression "storage stability" and refers to the capability of the liquid starter culture to substantially retain its initial metabolic activity during storage or extended periods of time under appropriate conditions.

As mentioned above, one characteristic of the liquid starter culture of the invention is its capability to retain its initial metabolic activity during storage under appropriate conditions. In preferred embodiments the liquid starter culture is stored at a temperature of −20° C. or higher, such as −10° C. or higher, e.g. −5° C. or higher, such as 0° C. or higher including 5° C. or higher, such as 10° C. or higher.

As it is shown in the below Examples, the liquid starter culture can be stored for a considerable period of time. Thus, the liquid starter culture according to the invention may be stored under the above conditions for at least 1 week or longer, such as at least 3 weeks or longer such as at least for 4 weeks or longer, e.g. 5 weeks or longer including 6 weeks or longer such as 7 weeks or longer. In a highly convenient embodiment, the starter culture according to the invention may be stored under the above conditions for at least 8 weeks or longer, such as at least 12 weeks or longer including at least 16 weeks or longer.

The liquid starter culture according to the invention is based on the surprising finding that a liquid starter culture can retain its initial metabolic activity during storage for a considerable period of time when a compound having a stabilising effect is added to the liquid starter culture at the starter culture production site. In presently preferred embodiments, a stabilising compound which is useful in the liquid starter culture according to the invention is a compound selected from the group consisting of formic acid, a formate, inosinate (IMP), serine and a compound involved in the biosynthesis of nucleic acids, including adenosine-5'-monophosphate (AMP), guanosine-5'-monophosphate (GMP), uranosine-5'-monophosphate (UMP), cytidine-5'-monophosphate (CMP), adenine, guanine, uracil, cytosine, adenosine, guanosine, uridine, cytidine, hypoxanthine, xanthine, hypoxanthine, orotidine, thymidine, inosine and a derivative of any of such compounds.

In a preferred embodiment of the invention the liquid starter culture contains formate at an amount which is less than 10% by weight. It is, however, preferred to add the stabilising compound at an amount which is in the range of 0.015% to 9% by weight, e.g. within the range of 0.1% to 8% by weight, such as within the range of 0.2% to 7% by weight, e.g. within the range of 0.3% to 5% by weight, such as within the range of 0.5% to 2% by weight, including within the range of 1% to 1.5% by weight.

Additionally, the liquid starter culture may contain further conventional additives including nutrients such as yeast extract, sugars and vitamins or other substances enhancing and/or stabilising the metabolic activity and/or viability of the starter culture organisms and/or one or more compounds for lowering the freezing point of the starter culture. Thus, in useful embodiments of the invention, the liquid starter culture further comprises at least one compound that has a metabolic activity stabilising effect selected from the group consisting of a sugar alcohol including glycerol, carbohydrates including ascorbic acid, disaccharides including sucrose and trehalose, vitamins, antioxidants, inert gases and surfactants including Tween® compounds.

In certain preferred embodiments, the liquid starter culture according to the invention contains sugar alcohols such as glycerol at an amount which is within the range of 5% to 40% by weight, e.g. as within the range of 10% to 35% by weight, including the range of 15% to 20% by weight. In a further embodiment the liquid starter culture contains disaccharides including sucrose at an amount which is within the range of 1% to 20% by weight, e.g. within the range of 5% to 15% by weight, including the range of 10% to 12% by weight. The liquid starter culture may also contain trehalose at an amount which is within the range of 0.5 M to 1.5 M, e.g. within the range of 0.7 M to 1.2 M, including the range of 0.8 M to 1 M. In useful embodiments, the liquid starter culture contains carbohydrates, vitamins and/or antioxidants, including natural antioxidants such as vitamin C (ascorbic acid) vitamin E and lecithins and chemical antioxidants such as ascorbyl palmitate, propyl-, octyl- or dodecyl-gallat, BHA (butylhydroxyanisole) and BHT (butylhydroxytoluene). Such compounds are useful in an amount within the range of 0.01% to 1% by weight, e.g. within the range of 0.05% to 0.8% by weight, including the range of 0.1% to 0.5% by weight. Surfactants including Tween® compounds, such as Tween®20, Tween®60 and Tween®80 may be added at an amount which is within the range of 0.1% to 2% by weight, e.g. within the range of 0.5% to 1.5% by weight, including the range of 0.8% to 1% by weight.

It is convenient to provide the liquid starter culture according to the invention as a starter culture concentrate both when used in food and feed production or for the production of metabolites that are generated by the starter culture strains. Typically, such a concentrate contains the starter culture organisms as a non-concentrated fermentate of the respective starter culture strain(s) or in a concentrated form. Accordingly, the starter culture of the invention may have a content of viable cells (colony forming units, CFUs) which is at least $10^8$ CFU per ml, e.g. at least $10^9$ CFU per ml, such as at least $10^{10}$ CFU per ml including at least $10^{11}$ CFU per ml, e.g. at least $10^{12}$ CFU per ml.

It will be understood that the liquid starter culture according to the invention can be provided as a frozen or dried, such as e.g. freeze-dried or spray-dried, starter culture as the starting material for the preparation of the liquid starter culture of the invention. Thus, it may be convenient to provide the starter culture as a frozen or dried culture and to thaw and, if required, to rehydrate the starter culture.

In accordance with the invention, any starter culture organism which is of use in the food or feed industry including the dairy industry can be used. Thus, the starter culture can be selected from a lactic acid bacterial species, a Bifidobacterium species, a Brevibacterium species, a Propionibacterium species or a fungal species such as a Torula species a Penicillium species, a Cryptococcus species and a Saccharomyces species. Suitable cultures of the lactic acid bacterial group include commonly used strains of a Lactococcus species, a Streptococcus species, a Lactobacillus species include the *Lactobacillus acidophilus*, Enterococcus species, Pediococcus species, a Leuconostoc species and Onescoccus species. Lactococcus species include the widely used *Lactococcus lactis*, including *Lactococcus lactis* subsp. *lactis* and *Lactococcus lactis* subsp. *cremoris* which are commonly used in the manufacture of cheeses with a closed texture, e.g. Cheddar, Feta and cottage cheese.

It will be appreciated, that the starter culture organism can be selected from a genetically modified strain of one of the above lactic acid bacterial strains or any other starter culture strain. As used herein the expression "genetically modified bacterium" is used in the conventional meaning of that term i.e. it refers to strains obtained by subjecting a lactic acid bacterial strain to any conventionally used mutagenization treatment including treatment with a chemical mutagen such as ethanemethane sulphonate (EMS) or N-methyl-N'-nitro-N-nitroguanidine (NTG), UV light or to spontaneously occurring mutants, including classical mutagenesis. Futhermore it is possible to provide the genetically modified bacterium by random mutagenesis or by selection of spontaneously occurring mutants, i.e. without the use of recombinant DNA-technology, it is envisaged that mutants of lactic acid bacteria can be provided by such technology including site-directed mutagenesis and PCR techniques and other in vitro or in vivo modifications of specific DNA sequences once such sequences have been identified and isolated.

As it is usual in the dairy industry, the starter culture may comprise a mixture of strains including a mixture of strains of different lactic acid bacterial species, such as e.g. a mixture of *Streptococcus thermophilus* and *Lactobacillus delbrueckii* subsp. *bulgaricus*.

The selection of strains for the starter culture of the invention will depend on the particular type of fermented food or feed product to be manufactured. Thus, e.g. for cheese and butter manufacturing, mesophilic cultures of Lactococcus species, Leuconostoc species and Lactobacillus species are widely used, whereas for yoghurt and other fermented milk products, thermophilic strains of Streptococcus species and of Lactobacillus species are typically used.

Fungal cultures are another group of microbial starter cultures, which may be used in accordance with the invention. Fungal cultures, such as yeast cultures and cultures of filamentous fungi, are commonly used in the manufacture of certain types of cheese and beverage. Examples of currently used cultures of fungi include *Penicillium roqueforti, Penicillium candidum, Geotrichum candidum, Torula kefir, Saccharomyces kefir* and *Saccharomyces cerevisiae*.

In a further aspect, the invention provides a liquid starter culture capable of retaining at least 50% of its initial metabolic activity at a temperature of −20° C. or higher for 1 week or more, said culture comprising at least one compound selected from the group consisting of a sugar alcohol including glycerol, carbohydrates including ascorbic acid, disaccharides including sucrose and trehalose, vitamins, antioxidants, inert gases and surfactants including Tween® compounds. It is, however, preferred that the liquid starter culture retains at least 60% of its initial metabolic activity, e.g. at least 70% including at least 80% such as at least 90% of its initial metabolic activity. In preferred embodiments the liquid starter culture is capable of retaining its initial metabolic activity when stored at a temperature of −20° C. or higher, such as −10° C. or higher, e.g. −5° C. or higher, such as 0° C. or higher including 5° C. or higher, such as 10° C. or higher.

As mentioned above and as it is shown in the below Examples, the liquid starter culture can be stored for a considerable period of time. Thus, the liquid starter culture according to the invention may be stored under the above conditions for at least 1 week or longer such as at least 3 weeks or longer such as at least for 4 weeks or longer, e.g. 5 weeks or longer including 6 weeks or longer such as 7 weeks or longer. In a highly convenient embodiment, the starter culture according to the invention may be stored under the above conditions for at least 8 weeks or longer, such as at least 12 weeks or longer including at least 16 weeks or longer.

It will be understood that the metabolic activity stabilising compounds are added to the liquid starter culture at the starter culture production site or at the dairy plant, in an amount which is sufficient to obtain the desired stability of the culture and which is sufficient to maintain the starter culture in a liquid state at a temperature in the range of −20° C. to 0° C. However, in certain preferred embodiments, the liquid starter culture according to the invention contains sugar alcohols such as glycerol, disaccharides including sucrose or trehalose in the amounts specified above. In useful embodiments, the liquid starter culture contains carbohydrates, vitamins and/or antioxidants as specified above or surfactants including Tween® compounds in the amounts as specified above.

As mentioned above, it is convenient to provide the liquid starter culture according to the invention as a starter culture concentrate both when used in food and feed production or for the production of metabolites that are generated by the starter culture strains. The starter culture concentrate typically has a content of viable cells (colony forming units, CFUs) which is at least $10^8$ CFU per ml, e.g. at least $10^9$ CFU per ml, such as at least $10^{10}$ CFU per ml including at least $10^{11}$ CFU per ml, e.g. at least $10^{12}$ CFU per ml.

In accordance with the invention, any of the above-mentioned starter culture organisms which is of use in the food or feed industry including the dairy industry can be used in the liquid starter culture. Furthermore, any of the above-mentioned mixed cultures may be useful in the liquid starter culture.

It is also within the scope of the invention to provide a method of stabilising a liquid starter culture, the method comprising adding to the culture concentrate an effective amount of a metabolic activity stabilising compound whereby at least 50% of the initial metabolic activity of the culture concentrate is retained at a temperature of −20° C. or higher for 1 week or longer.

It is an advantageous feature of the method according to the invention that the above liquid starter culture is stable with respect to viability and metabolic activity including acid-producing activity for an extended period of time. Evidently, this feature implies that the method is very flexible in that the liquid starter culture can be supplied to the food or feed production plant, e.g. a dairy plant, and stored until the culture is needed. Conveniently, the liquid starter culture can be added directly to the substrate material, such as milk, meat, flour dough, wine and plant materials, such as vegetables, fruits or fodder crops. Accordingly, the use of liquid starter cultures has the advantage that no propagation, i.e. no preparation of a bulk starter at the dairy plant, of the starter organisms at the food or feed production site is necessary.

When used in accordance with the above method the stabilising compound, which is e.g. selected from the group consisting of formic acid, a formate, inosinate (IMP), serine and a compound involved in the biosynthesis of nucleic acids, including adenosine-5'-monophosphate (AMP), guanosine-5'-monophosphate (GMP), uranosine-5'-monophosphate (UMP), cytidine-5'-monophosphate (CMP), adenine, guanine, uracil, cytosine, adenosine, guanosine, uridine, cytidine, hypoxanthine, xanthine, hypoxanthine, orotidine, thymidine, inosine and a derivative of any of such compounds is conveniently added to the liquid starter culture at the production site of the starter culture. In one useful embodiment of the method according to the invention, the liquid starter culture contains formate at an amount that is less than 10% by weight including the above amounts of the stabilising compound. It is, however, preferred to add the stabilising compound at an amount which is within the range of 0.015% to 9% by weight, e.g. within the range of 0.1% to 8% by weight, such as the range of 0.2% to 7% by weight, e.g. the range of 0.3% to 5% by weight, such as the range of 0.5% to 2% by weight, including the range of 1% to 1.5% by weight.

In useful embodiments, the starter culture used in the method of the invention comprises at least one further compound having a metabolic activity stabilising effect selected from the group consisting of a sugar alcohol including glycerol, carbohydrates including ascorbic acid, disaccharides including sucrose and trehalose, vitamins, antioxidants, inert gases and surfactants including Tween® compounds. However, it will be appreciated that the above compounds are useful when used in the above-mentioned concentrations e.g. when the liquid starter culture in the method according to the invention is kept at temperatures below 0° C.

In an advantageous and highly convenient embodiment, the starter culture used in the method according to the invention is provided as a liquid starter culture concentrate. The use of a concentrate of the starter culture organisms involves the significant advantage over a non-concentrated liquid culture that it reduces the requirement for storage facilities significantly at the food or feed production site. Such a concentrate contains the starter culture organisms in a concentrated form, typically at a content of viable organisms of $10^{10}$ CFU per ml or higher including at least $10^{11}$ CFU per ml or higher, e.g. $10^{12}$ CFU per ml or higher.

In further aspects, the invention relates to a method of providing a liquid starter culture which is capable of retaining at least 50% of its initial metabolic activity at a temperature of −20° C. or higher for 1 week or more, said method comprising adding to the culture an amount of at least one compound selected from the group consisting of a sugar alcohol including glycerol, carbohydrates including ascorbic acid, disaccharides including sucrose and trehalose, vitamins, antioxidants, inert gases and surfactants including Tween® compounds, said amount being sufficient to maintain the starter culture in a liquid state at a temperature in the range of −20° C. to 0° C. It is, however, preferred that the liquid starter culture retains at least 60% of its initial metabolic activity, e.g. at least 70% including at least 80% such as at least 90% of its initial metabolic activity. In preferred embodiments the liquid starter culture is capable of retaining its initial metabolic activity when stored at a temperature of −20° C. or higher, such as −10° C. or higher, e.g. −5° C. or higher, such as 0° C. or higher including 5° C. or higher, such as 10° C. or higher.

It will be understood that the metabolic activity stabilising compounds are added to the liquid starter culture at the starter culture production site or at the dairy plant, in an amount which is sufficient to obtain the desired stability of the culture and which is sufficient to maintain the starter culture in a liquid state at a temperature in the range of −20° C. to 0° C. However, in useful embodiments, the liquid starter culture of the method according to the invention contains the metabolic activity stabilising compounds in the above-mentioned concentrations.

It is, however, convenient to provide the liquid starter culture of the method according to the invention as a starter culture concentrate both where used in food and feed production or for the production of metabolites that are generated by the starter culture strains. The starter culture concentrate typically has a content of viable cells (colony forming units, CFUs) which is at least $10^8$ CFU per ml, e.g. at least $10^9$ CFU per ml, such as at least $10^{10}$ CFU per ml including at least $10^{11}$ CFU per ml, e.g. at least $10^{12}$ CFU per ml.

In accordance with the invention, any of the above mentioned starter culture organisms which is of use in the food or feed industry including the dairy industry can be used in the liquid starter culture. Furthermore, any of the above-mentioned mixed culture may be useful in the liquid starter culture.

In a further aspect, the invention pertains to a method of preparing a food or a feed product said method comprising using the stabilised liquid starter culture according to the invention.

In a specific embodiment the food product is a milk-based product such as cheese, yoghurt, butter or a liquid fermented milk product, such as e.g. buttermilk or drinking yoghurt. Furthermore, the food product may be selected from a meat product, a vegetable product and a beverage such as wine and beer.

Another significant application of the method according to the present invention is the use of the liquid starter cultures as so-called probiotics. By the term "probiotic" is in the present context understood a microbial culture which, when ingested in the form of viable cells by humans or animals, confers an improved health condition, e.g. by suppressing harmful micro-organisms in the gastrointestinal tract, by enhancing the immune system or by contributing to the digestion of nutrients. A typical example of such a probiotically active product is "sweet acidophilus milk".

In further embodiments, the method according to the invention is used in the production of an animal feed such as silage e.g. grass, cereal material, peas, alfalfa or sugar-beet leaf, where bacterial cultures are inoculated in the feed crop to be ensiled in order to obtain a preservation hereof, or in protein rich animal waste products such as slaughtering offal and fish offal, also with the aims of preserving this offal for animal feeding purposes.

Typically, the starter organisms used in the method of preparing a food and feed product is added to the starting material at a concentration in the range of $10^5$ to $10^9$ CFU per ml or g of the material, such as at least $10^5$ CFU per ml or g of the material, including at least $10^6$ CFU per ml or g of the material, such as at least $10^7$ CFU per ml or g of the material, e.g. at least $10^8$ CFU per ml or g of the material, including at least $10^9$ CFU per ml or g of the starting material.

The invention is further illustrated in the following non-limiting examples and the drawings wherein FIG. 1 shows the activity of a liquid form of a commercial starter culture designated R-604 (Chr. Hansen A/S, Hørsholm, Denmark) comprising mesophilic *Lactococcus lactis* strains, with and without supplementation with Na-formate and/or IMP during storage at a temperature of 0° C. for 0 to 6 weeks;

Figure 4:
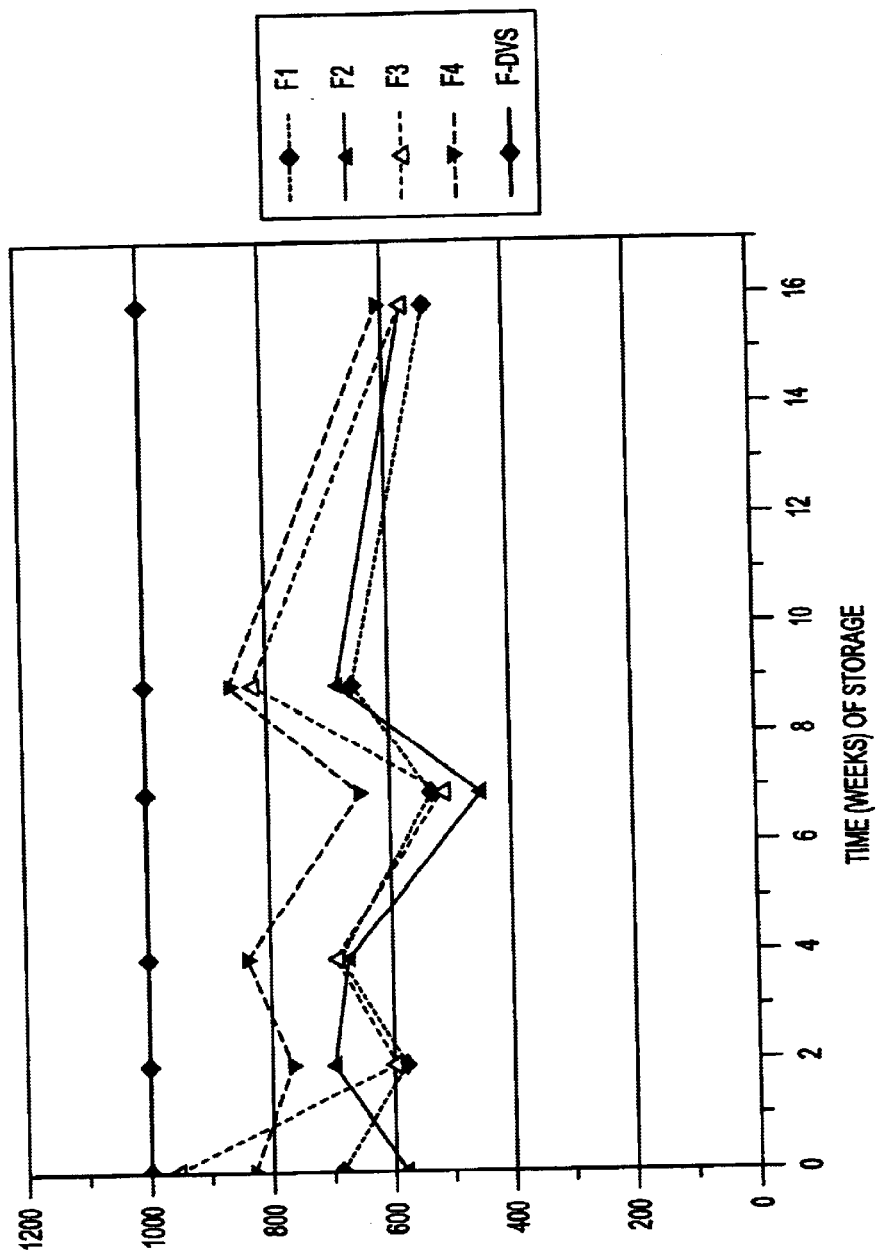
Figure 5:
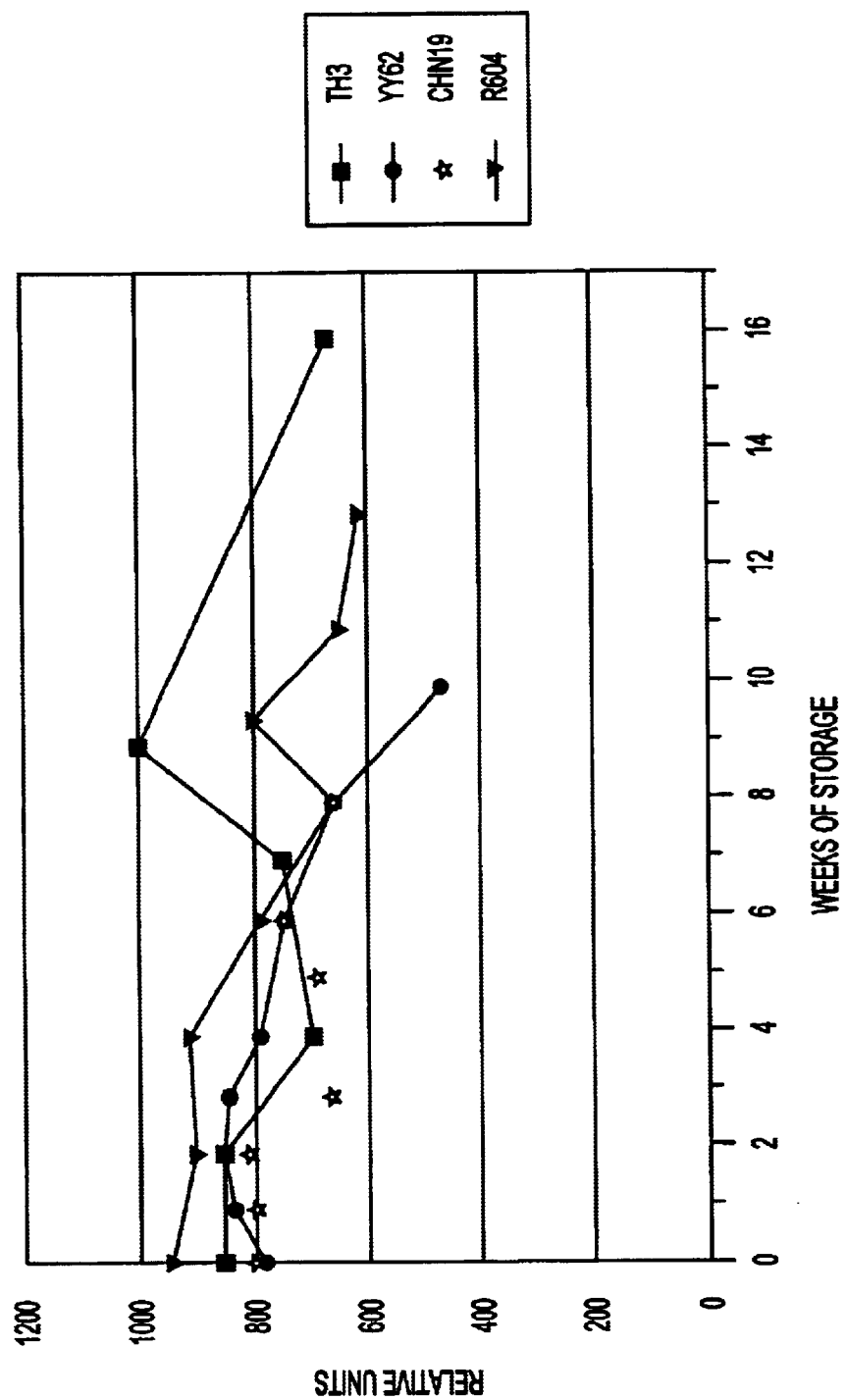

FIG. 4 shows the acid-producing activity of the commercial liquid starter culture TH-3 comprising a thermophilic *Streptococcus thermophilus* strain with supplementation with various compounds during storage at a temperature of −20° C. for up to 16 weeks; and FIG. 5 shows the acid-producing activity of the liquid starter cultures TH-3, YY62, CHN19 and R-604 with supplementation with various compounds during storage at a temperature of −20° C. for up to 16 weeks.

EXAMPLE 1

Study of the Stabilising Effect of Na-formate and IMP on the Storage Stability of Liquid Lactic Acid Bacterial Starter Culture Concentrates The stabilising effect of Na-formate, IMP or cryoprotective agents on the storage stability of liquid lactic acid bacterial starter culture concentrates was studied.

1.1 Bacterial Strains, Media and Methods

The following liquid concentrates of lactic acid bacterial strains were used in the example: the commercial R-604 and R-603 cultures comprising mesophilic *Lactococcus lactis* strains and the TH-4 culture comprising a thermophilic *Streptococcus thermophilus* strain.

The liquid starter culture concentrates were supplemented with the following compounds, respectively:

3% Na-formate

3% Inosinate (IMP)

3% Cryoprotective agents

The culture concentrate preparations were kept at a temperature of 0, 5 and 10° C., respectively, for up to 6 weeks. Starter culture concentrates without supplement were kept at a temperature of −50° C. and used as a reference.

Each week samples of the starter culture concentrate preparations were inoculated in pasteurised skimmed milk or in reconstituted skimmed milk (RSM) containing 9.5% solid matter heat treated at 135° C. for 8 sec.+99° C. for 30 min, and the inoculated skimmed milk and RSM were incubated under relevant temperature conditions to permit acidification of the substrate material. Samples were collected at appropriate points in time and the acidification activity was measured as described by Foldager (1994). In addition, the viable cell number (CFU) of each sample after cultivation was determined.

1.2 Results

Under the applied experimental conditions the addition of cryoprotective agents to the culture concentrate before storage had no influence on the storage stability, i.e. the metabolic activity, of the strains (data not shown). Table 1.1 summarises the general storage stability of liquid starter culture concentrate preparations.

TABLE 1.1

The general storage stabilising effects of Na-formate and/or IMP on liquid starter culture concentrate

| Culture | Temperature | Stability |
|---|---|---|
| R-604 | 0° C. | 5 to 6 weeks |
|  | 5° C. | approximately 3 weeks |
|  | 10° C. | approximately 1 week |
| R-603 | 0° C. | 5 to 6 weeks |
|  | 5° C. | approximately 3 weeks |
|  | 10° C. | less than 1 week |
| TH-4 | 0° C. | approximately 3 weeks |
|  | 5° C. | approximately 3 weeks |

Figure 1:
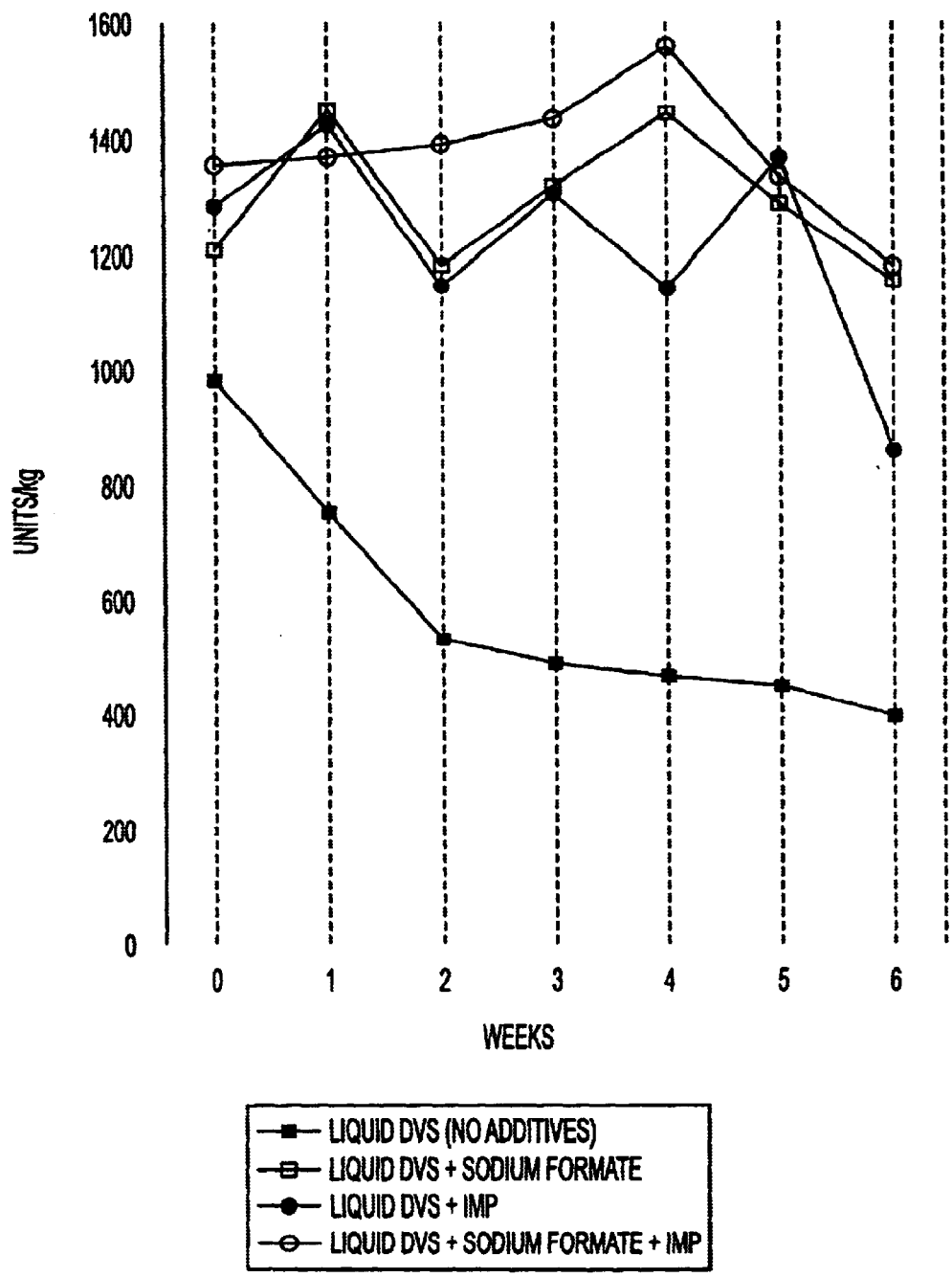
Figure 2:
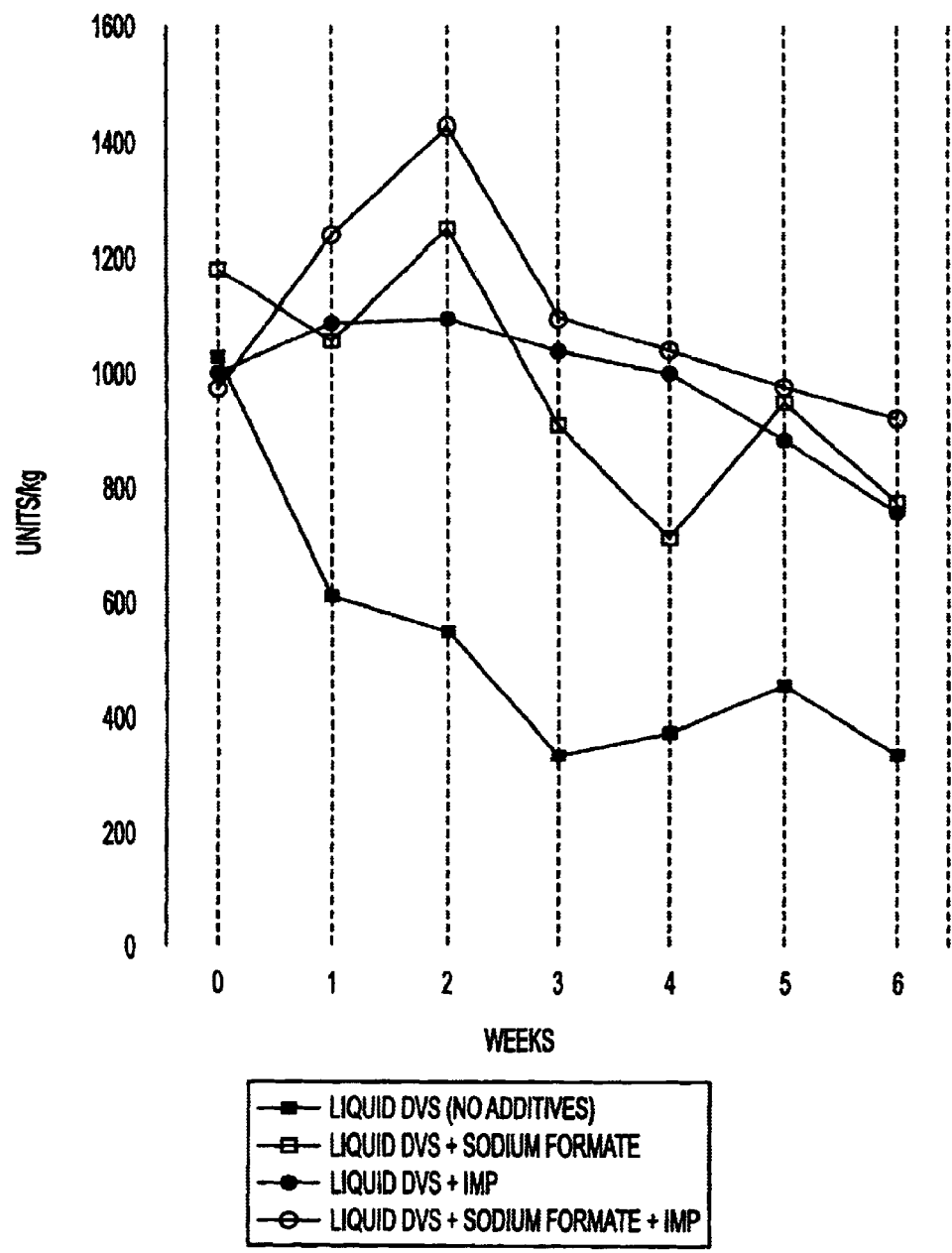
FIG. 2 shows the activity of a liquid commercial starter culture designated R-603 (Chr. Hansen A/S, Hørsholm, Denmark) comprising mesophilic *Lactococcus lactis* strains, with and without supplementation with Na-formate and/or IMP during storage at a temperature of 0° C. for 0 to 6 weeks.
Figure 3:
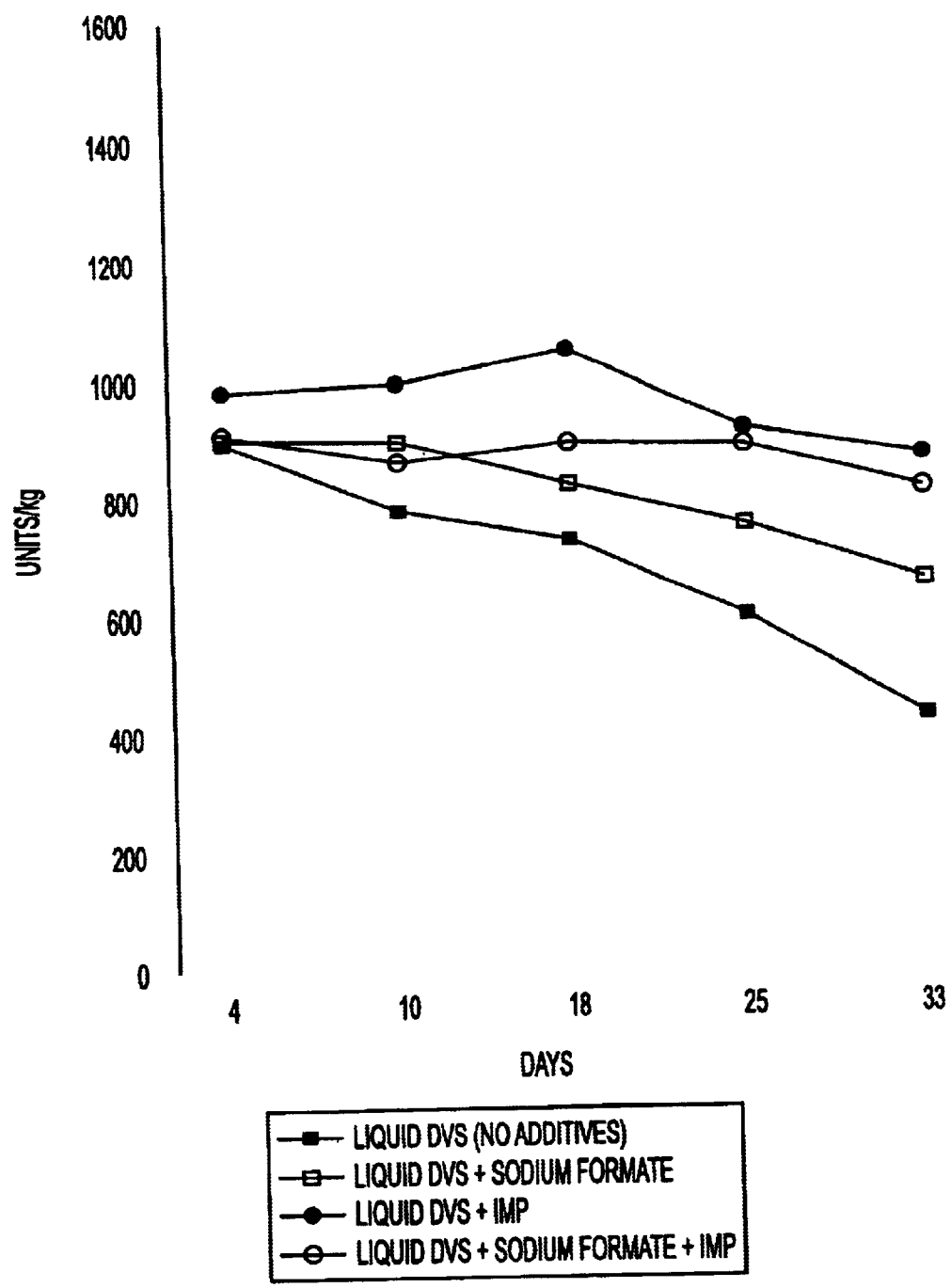
FIG. 3 shows the activity of a liquid form of a commercial starter culture designated TH-4 (Chr. Hansen A/S, Hørsholm, Denmark) comprising a thermophilic *Streptococcus thermophilus* strain, with and without supplementation with Na-formate and/or IMP during storage at a temperature of 0° C. for 0 to 6 weeks.

The results of the activity measurements during storage at a temperature of 0° C. are summarized in FIGS. 1, 2 and 3 for the starter culture concentrate preparations of the cultures R-604, R603 and TH-4, respectively. The activity of the frozen reference cultures has been defined as 1000 units/kg. The initial acid-producing activity of the culture concentrate preparations is above 1000 units/kg assumingly due to an activity-stimulating effect of Na-formate and IMP on the microbial culture.

The results shown in FIG. 1 clearly demonstrate that strains of R-604 were capable of retaining their initial acid-producing activity during storage at a temperature of 0° C. for 5 to 6 weeks. Likewise, there is only minor loss of the initial acid-producing activity of strains of the R-603-culture during storage at 0° C. for 5 to 6 weeks. FIG. 3 shows that strains of the TH4-culture are capable of being stored at 0° C. for 3 weeks without loss of initial acid-producing activity. After 6 weeks of storage the loss of the initial acid-producing activity is only about 10%.

1.4 Conclusion

This Example shows that Na-formate and/or IMP has an effect on the storage stability of liquid lactic acid bacterial starter culture concentrates as the addition of the compounds to the concentrates results in that the starter cultures retain their initial acid-producing activity for about 5 to 6 weeks when kept at a temperature of 0° C.

EXAMPLE 2

The Effect of Storage of a Stabilised Liquid Mesophilic Starter Culture on its Activity in Cheese Making on an Industrial Scale The effect of storage on the activity of a liquid starter culture was studied in a cheese making trial on an industrial scale.

1. Bacterial Strains, Media and Methods

The following starter culture concentrates of lactic acid bacterial strains were used in this experiment: the commercial frozen F-DVS 604 p2104250 starter culture and a liquid starter culture of R-604 comprising mesophilic *Lactococcus lactis* strains. The liquid starter culture originated from the same large scale production as the frozen starter culture.

The liquid starter culture concentrate was supplemented with a 6% of a 50% solution of sodium formate and stored at 0° C. for about 4 weeks.

The cheese trials were performed at Malpass, UK, in a 1,000 liters cheese vat. A standard Cheddar recipe was used for the production of the cheese (see Table 2.1). Frozen F-DVS 604 starter culture was used as a control. The trials were performed in duplicate.

From each cheese vat 4 cheeses of about 20 kg were made, which after 24 hours were placed in a storage room at 8° C. or 10° C. Samples were taken after 24 hours of storage and subjected to chemical analyses, i.e. measurement of pH of the cheese and the water, fat and salt content of the cheese.

TABLE 2.1

Cheese making parameters and results of the cheese trial

| Parameter | Standard recipe | Vat 1 F-DVS 604 Actual I | Vat 1 F-DVS 604 Actual II | Vat 2 Liquid culture of 604 Actual I | Vat 2 Liquid culture of 604 Actual II |
|---|---|---|---|---|---|
| Repeat No. | recipe | I | II | I | II |
| Milk temperature | 32° C. | 29.5 | 31.5 | 29.9 | 31.0 |
| Milk pH |  | 6.64 | 6.64 | 6.64 | 6.64 |
| Milk volume | 1000 l | 804 kg | 806 kg | 806 kg | 797 kg |
| Starter culture added | R-604 | F-DVS 604 | F-DVS 604 | Liquid 604 | Liquid 604 |
| Starter culture added, amount | 150 g | 140 g | 140 g | 140 g | 140 g |
| Ripening time | 40 min | 30 min | 30 min | 30 min | 30 min |
| Rennet added |  | Chymax 190, 145 g | Chymax ultra, 39 g | Chymax 190, 145 g | Chymax ultra, 39 g |
| Rennet added, time |  | 11:50 | 10:30 | 12:20 | 10:00 |
| Set Time | 40 min | 48 min | 40 min | 45 min | 40 min |
| Cutting time |  | 12:38 | 11:10 | 13:05 | 10:40 |
| Scalding start |  | 12:50 | 11:20 | 13:18 | 10:50 |
| Scalding temp. | 40.5 | 40.7 | 40.3 | 41.0 | 40.8 |
| Scalding time | 45 min | 45 min | 40 min | 45 min | 35 min |
| Pitch time |  | 14:0 | 12:40 | 14:30 | 12:10 |
| Rennet to pitch | 2 h 15 min | 2 h 10 min | 2 h 10 min | 2 h 10 min | 2 h 10 min |
| Whey off, TA % |  | 0.1 | 0.11 | 0.1 | 0.11 |
| Milling, time |  | 15.50 | 14:30 | 16:15 | 14:00 |
| Mill TA % | 0.45 | 0.43 | 0.41 | 0.46 | 0.45 |
| Rennet to mill | 3 h 50 min | 4 h 00 min | 4 h 00 min | 3 h 55 min | 4 h 00 min |
| Composition of 24 hours cheese |  | Fat: 33% Moisture: 36.03% Salt: 2.4% pH: 5.57 | Fat: 33% Moisture: 36.7% Salt: 2.2% pH: 5.54 | Fat: 34% Moisture: 37.27% Salt: 1.5% pH: 5.38 | Fat: 34% Moisture: 35.99% Salt: 2.4% pH: 5.5 |

2.2 Results

The parameters for the cheese trial and the results are shown in Table 2.1 above. As it appears, the activity of the liquid starter culture was as good or even slightly better compared to the frozen commercial starter culture F-DVS 604. The better acidification results when using the liquid culture are obtained even though the liquid cultures are slightly diluted with sodium formate, and consequently contain a correspondingly lower cell count compared to the control starter culture.

The rennet to mill were obtained in about 4 hours for both starter cultures, however the liquid starter culture had a slightly higher acidity at milling. The compositions of the cheeses produced are given in Table 2.1.

2.3 Conclusion

This industrial trial shows that the addition of sodium formate to a liquid starter culture concentrate has an effect on the storage stability of the culture as the addition of the compound to the liquid culture concentrate results in that the starter culture has retained its initial acid-producing activity for about 4 weeks when kept at a temperature of 0° C. The liquid starter culture shows the same activity after storage as commercial, frozen starter culture, and thus is very useful in the cheese industry.

EXAMPLE 3

The Effect of Storage of a Stabilised Liquid Thermophilic Starter Culture on its Activity in Cheese Making on an Industrial Scale The purpose of this trial was to compare the activity of the liquid thermophilic starter culture DVS TH-4, which was kept at 0° C. for 4–5 weeks before testing, with the frozen DVS TH-4 from the same batch fermentation (batch 2108513). The trial was carried out in Italian pizza cheese at the dairy Ambrosi S.p.A., Castenedolo, Italy.

3.1 Bacterial Strains, Media and Methods

The following starter culture concentrates of lactic acid bacterial strains were used in this experiment: the commercial frozen F-DVS TH-4 starter culture comprising thermophilic *Streptococcus thermophilus* strains and a liquid starter culture DVS of TH-4. The liquid starter culture originated from the same large-scale production (batch 2108513) as the frozen starter culture.

The liquid starter culture concentrate was supplemented with a 6% of a 50% solution of sodium formate and stored at 0° C. for about 4–5 weeks.

The starter cultures concentrate were inoculated in milk, having the following parametres:

| | |
|---|---|
| Fat content | 3.20 |
| Protein content | 3.16 |
| Lactose | 4.74 |
| pH of the fresh milk | 6.50 |

Citric acid was used to decrease pH of the milk before adding the starter culture and rennet. The dosage of citric acid was about 2.3 kg per 5000 liters. The citric acid was diluted in cold water and then added to the milk. pH before adding the rennet was 6.15 to 6.20.

The cheese trail was performed in a 5000 liters cheese vat using 500 g starter culture for inoculation. The cheese vat was a CMT vat of 5000 liters with horizontal stirring and cutting. Stainless steel wires were used for the cutting and stirring.

The recipe used for the production of Italian pizza Mozzarella cheese (Table 3.1). Frozen F-DVS TH-4 starter culture was used as a control (batch 2108513).

For pizza Mozzarella the cheese blocks (1 kg each) are brine salted up to 1.5% salt and then vacuum packed.

TABLE 3.1

The recipe for the production of Italian pizza Mozzarella cheese

| | |
|---|---|
| Filling time | 30 min |
| Temperature of the milk | 36–37° C. |
| Citric acid | 2.3 kg/5000 liters |
| Culture inoculation | Beginning of filling, 500 g/5000 liters |
| Renneting time | 15 min |
| Cutting/stirring | 45 min |
| Draining | 15 min |

TABLE 3.1-continued

The recipe for the production of Italian pizza Mozzarella cheese

| | |
|---|---|
| To cheese table | pH 6.10 |
| Total draining | pH 5.5–5.7 |
| Stretching at pH | pH 5.20 |
| Stretching water temp. | 80–85° C. |
| Cheese curd temperature | 53–55° C. |
| From inoculation to stretch | 2½ to 3 hours. |

3.2 Results

Table 3.2 shows the fermentation for the frozen and the liquid form of the commercial starter culture designated TH-4 (Chr. Hansen A/S, Hørsholm, Denmark) comprising a thermophilic *Streptococcus thermophilus* strain. As described above, the liquid starter culture was supplemented with sodium-formate during storage at a temperature of 0° C. for 4–5 weeks. From each vat whey, samples were taken and subjected to chemical analyses, i.e. measurement of fat, protein and lactose content of the cheese.

TABLE 3.2

Results of the cheese trial

| | TH-4 liquid (500 ml) vat 14 | | TH-4 F-DVS (500 g) vat 15 (control) | | TH-4 liquid (500 ml) vat 16 | |
|---|---|---|---|---|---|---|
| | pH | Time (min) | pH | Time (min) | pH | Time (min) |
| Filling | 6.20 | 0 | 6.20 | 0 | 6.20 | 0 |
| Culture | 6.20 | 5 | 6.20 | 5 | 6.20 | 5 |
| Rennet | 6.15 | 35 | 6.18 | 35 | 6.20 | 35 |
| Cutting | 6.15 | 50 | 6.15 | 50 | 6.15 | 55 |
| Draining | 6.10 | 95 | 6.05 | 90 | 6.00 | 100 |
| Cheese table | 5.95 | 110 | 6.00 | 105 | 5.86 | 115 |
| pH | 5.65 | 150 | 5.90 | 115 | 5.78 | 130 |
| pH | 5.53 | 160 | 5.70 | 135 | 5.63 | 135 |
| pH | 5.35 | 175 | 5.56 | 150 | 5.45 | 150 |
| pH | 5.26 | 190 | 5.38 | 165 | | |
| Stretching | 5.20 | 195 | Cooled down | | Cooled down | |
| Whey composition | Fat 0.36 Protein 1.08 Lactose 5.08 | | Fat 0.40 Protein 1.10 Lactose 4.98 | | Fat 0.44 Protein 1.02 Lactose 5.08 | |

Vat no. 15 and 16 were cooled down by adding cold water to the cheese table. Due to lack of stretching capacity they had to be stretched the following day.

As it appears from Table 3.2, the activity of the liquid starter culture was as good or even a slightly better compared to the frozen commercial starter culture F-DVS TH-4.

3.3 Conclusion

This industrial trial shows that the addition of sodium formate to a liquid starter culture concentrate has an effect on the storage stability of the culture as the addition of the compound to the liquid culture concentrate results in that the starter culture has retained its initial acid-producing activity for about 4–5 weeks when kept at a temperature of 0° C. The liquid starter culture shows the same activity after storage as commercial, frozen starter culture.

EXAMPLE 4

Study of the Stabilising Effect of Various Compounds on the Storage Stability of Liquid Lactic Acid Bacterial Starter Culture Concentrates The objective of this study was to obtain a bacterial liquid starter culture, which is capable of retaining its initial acid-producing activity when stored for at least 3 month.

The storage temperature in this study was −20° C. in order to prolong the stability.

The stabilising effect of glycerol, sucrose, nitrogen, ascorbic acid and Tween®80 on the storage stability of a liquid lactic acid bacterial starter culture concentrate was studied.

4.1 Bacterial Strains and Methods 4.1.1 Bacterial Strains

The following liquid culture concentrates of commercial lactic acid bacterial strains were used in this study: The TH-3 culture comprising thermophilic *S. thermophilus*, the R-604 culture comprising mesophilic *L. lactis*, the CH-N19 culture is a mixed culture of mesophilic strains and the YY62 culture comprising a mixture of 2 different *L. lactis* spp *lactis* strains (14.4 and 42%), *L. lactis* spp *cremoris* (21%), Leoconostoc (7.4%) and *S. thermophilus* (14.4%).

4.1.2 Storage Solutions

In order to stabilise the cells during storage several compounds were tested in various combinations as shown in Table 4.1 using the cultures TH-3 (FIG. 4) and CH-N19. In the following experiments with the cultures R-604 and YY62 only the solution showing the most stabilising effect, named F4, was used (FIG. 5). The storage solutions were kept at −20° C.

TABLE 4.1

The storage solutions (F1–F4) used.
The added compounds are shown in W/vol.

| Solutions | F1 | F2 | F3 | F4 |
|---|---|---|---|---|
| Na formate 2% | + | + | + | + |
| glycerol 35% | + | + | + | + |
| sucrose 12% | | | | + |
| head space N$_2$ | + | + | | + |
| ascorbic ac. 0.1% | + | | + | + |
| Tween ®80 0.8% | + | + | + | + |
| trehalose 1M | | | | |
| grindox 1% | | | | |
| TH-3 conc. 52% | + | + | + | + |
| dilution water to 100% | + | + | + | + |

4.1.3 Methods

Inoculation and Activity Test 100 and 200 ml bottles of reconstituted skimmed milk (RSM) containing 9.5% solid matter heat treated at 135° C. for 8 sec.+99° C. for 30 min, was prepared one day in advance and kept at 5° C. until use. The storage solutions of the liquid starter culture of TH-3 (kept at −20° C.) and the frozen starter culture of TH-3 (stored at −50° C.) were kept at 5° C. before inoculation.

The milk was inoculated with 0.01% of the storage solutions F1 to F4. The inoculation was performed at 5° C. and the bottles were hereafter placed in pre-warmed water bath at 37° C. with the calibrated pH electrodes connected to the data logger. The pH measuring was continued for at least 16 hours, and pH after 4 hours incubation was used for comparison of samples and for calculating the acid-producing activity (in units/kg) of the samples. The pH of the samples was compared with the pH of the frozen pellets, which activity has been defined as 1000 units (as reference).

4.3. Results and Discussion

FIGS. 4 and 5 show clearly that the addition of compounds such glycerol, sucrose, nitrogen, Tween®80 and ascorbic acid to liquid starter culture concentrates has an effect on the storage stability of the culture as the addition of the compounds to the liquid culture concentrates results in that the starter cultures have retained their initial acid-producing activity for about 2–3 months when kept at a temperature of −20° C. The liquid cultures of TH-3 and R-604 were capable of retaining their initial acid-producing activity during storage for approximately 3 months and the liquid culture of YY62 for approximately 2 months. Gas chromatography and High performance liquid chromatography (HPLC) analysis of the YY62 samples show that all the relevant components such as acetaldehyd, α-acetolactate, diacetyl, acetoin and butanediol are produced during fermentation (data not shown) showing that the metabolic activity in general is intact.

REFERENCE

Foldager, L. 1994. Determination of acidification activity in F-DVS by the LF method. Analytical Procedure Q-Ap-039.dk, Chr. Hansen A/S.

What is claimed is:

1. A liquid starter culture comprising 0.1 to 8% by weight of at least one compound that has a stabilizing effect on at least one metabolic activity of the liquid starter culture, so that, during storage of the liquid starter culture in liquid state at a temperature in the range of −20° C. to 10° C. for 1 week or more, at least 50% of at least one initial metabolic activity is retained, said metabolic activity comprising at least one of oxygen removal activity, acid producing activity and metabolite producing activity, said at least one compound being selected from the group consisting of formic acid, a formate, and a derivative of any of said at least one compound.

2. The liquid starter culture according to claim 1, which also comprises at least one compound capable of lowering the freezing point of the starter culture.

3. The liquid starter culture of claim 1, further comprising at least one compound selected from the group consisting of a sugar alcohol, a carbohydrate, a disaccharide, a vitamin, an antioxidant, an inert gas and a surfactant.

4. The liquid starter culture of claim 1 where the liquid starter culture is provided as a starter culture concentrate.

5. The liquid starter culture of claim 1 comprising at least $10^8$ CFU of starter culture organisms.

6. The liquid starter culture of claim 1 wherein a liquid starter culture organism is selected from the group consisting of Bifidobacterium spp., Brevibacterium spp., Propionibacterium spp., Lactococcus spp., Lactobacillus spp., Streptococcus spp., Enterococcus spp., Pediococcus spp., Leuconostoc spp., Oenococcus spp. and fungal spp.

7. A method of preparing a food or a feed product, said method comprising inoculating a food or feed material with a stabilised liquid starter culture according to any of claims 1–6 and incubating the inoculated material under conditions permitting the liquid starter culture to become metabolically active.

8. The method of claim 7 wherein the food product comprises a milk based product, a meat product, a vegetable product or a beverage.

9. The method of claim 7 wherein the inoculation of the food material is made directly by connecting a container containing the stabilized, liquid starter culture to a food process line.

10. A liquid starter culture of claim 1 which has not been frozen.

11. The liquid starter culture of claim 1 which is contained in a commercial packaging.

12. The liquid starter culture of claim 1 where at least 70% of the at least one initial metabolic activity is retained.

13. The liquid starter culture of claim 1 where the at least 50% of the at least one initial metabolic activity is retained for at least 3 weeks.

14. The liquid starter culture of claim 3 where the sugar alcohol is glycerol.

15. The liquid starter culture of claim 3 where the carbohydrate is ascorbic acid.

16. The liquid starter culture of claim 3 where the disaccharide is selected from the group consisting of sucrose and trehalose.

17. The liquid starter culture of claim 3 where the surfactant is a Tween® compound.

18. The liquid starter culture of claim 6 where the Lactococcus spp. is selected from the group consisting of *Lactococcus lactis* subsp. *lactis* and *Lactococcus lactis* subsp. *cremoris.*

19. A method of proving a commercial microbial starter culture in liquid state to a site of food or feed manufacturing, the method comprising providing the stabilized culture of any of claims 1–6 and distributing it to said food or feed manufacturing site.

20. A method of preparing a stabilized liquid starter culture, the method comprising adding to a liquid starter culture 0.1 to 8% by weight of at least one compound that has a stabilizing effect on at least one metabolic activity of the liquid starter culture, said at least one compound being selected from the group consisting of formic acid, a formate, and a derivative of any of said at least one compound, so that, during storage of the liquid starter culture in liquid starter at a temperature in the range of −20° C. to 10° C. for 1 week or more, at least 50% of at least one initial metabolic activity of the liquid starter culture is retained, said at least one metabolic activity comprising at least one of oxygen removal activity, acid producing activity and metabolite producing activity, and packaging the thus obtained stabilized liquid starter culture in a commercial packaging for distributing the culture to a site of production.

21. The method of claim 20 comprising adding at least one further compound selected from the group consisting of a sugar alcohol, a carbohydrate, a disaccharide, a vitamin, an antioxidant, an inert gas and a surfactant.

22. The method of claim 20 wherein the liquid starter culture is provided as a starter culture concentrate.

23. The method of claim 20 wherein a liquid starter culture organic is selected from the group consisting of Bifidobacterium spp., Brevibacterium spp., Propionibacterium spp., Lactobacillus spp., Lactobacillus spp., Streptococcus spp., Enterococcus spp., Pediococcus spp., Leuconostoc spp., Oenococcus spp. and fungal spp.

24. The method of claim 20 wherein the liquid starter culture is packaged in a commercial packaging that can directly connected to a process line.

25. A method of claim 20 further comprising adding to the liquid starter culture at least one compound capable of lowering the freezing point of the liquid starter culture.

26. A liquid starter culture comprising 0.1 to 8% by weight of at least one compound selected from the group consisting of formic acid, a formate, and a derivative of any of such at least one compound.

* * * * *

UNITED STATES PATENT AND TRADEMARK OFFICE
CERTIFICATE OF CORRECTION

PATENT NO.   : 6,787,348 B1
DATED        : September 7, 2004
INVENTOR(S)  : Kringelum et al.

It is certified that error appears in the above-identified patent and that said Letters Patent is hereby corrected as shown below:

<u>Title page,</u>
Item [73], Assignee, replace "CHR. Hansen" with -- Chr. Hansen A/S --.

Signed and Sealed this

Twenty-fifth Day of April, 2006

JON W. DUDAS
*Director of the United States Patent and Trademark Office*